(12) United States Patent
Koche et al.

(10) Patent No.: US 7,338,964 B2
(45) Date of Patent: Mar. 4, 2008

(54) 2-SUBSTITUTED-1-DEAZA PURINE DERIVATIVES WITH ADENOSINE RECEPTOR MODULATING ACTIVITY

(75) Inventors: Melle Koche, Weesp (NL); Jacobus A. J. den Hartog, Weesp (NL); Martinus J. Wanner, Weesp (NL); Gerrit-Jan Koomen, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 0 days.

(21) Appl. No.: 11/219,817

(22) Filed: Sep. 7, 2005

(65) Prior Publication Data

US 2006/0052412 A1    Mar. 9, 2006

Related U.S. Application Data

(60) Provisional application No. 60/608,145, filed on Sep. 9, 2004.

(51) Int. Cl.
C07D 471/02    (2006.01)
C07D 491/02    (2006.01)
C07D 498/02    (2006.01)
A01N 43/42     (2006.01)
A61K 31/44     (2006.01)

(52) U.S. Cl. ...................... 514/303; 546/118
(58) Field of Classification Search ............... 546/118; 514/303
See application file for complete search history.

(56) References Cited

U.S. PATENT DOCUMENTS 4,977,144 A * 12/1990 Fujimoto et al. ............ 514/45

FOREIGN PATENT DOCUMENTS

| EP | 354180 | * | 7/1989 |
| EP | 0 354 180 A2 | | 2/1990 |
| JP | 2004-217582 | | 5/2004 |
| WO | WO 2002/31176 A1 | | 4/2002 |
| WO | WO 2004/069185 A2 | | 8/2004 |
| WO | WO 2006/027366 A1 | | 3/2006 |

OTHER PUBLICATIONS

Holy et al., J. Med.Chem., "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base", 1999, vol. 42, pp. 2064-2986.*
Francis et al., Canadian Journal of Chemistry, "A general synthesis of 5,7-diaminoimidazo[4,5-b]pyridine ribosides ("2-amino-1-deazaadenosines") from 5-amino-4-imidazolecarboxamide riboside (AICA riboside)", 1992, vol. 70, pp. 1288-1295.*
Hess et la., Expert Opin. Ther. Patents, "Recent advances in adenosine receptor antagonist research", 2001, vol. 11, pp. 1533-1561.*
Baraldi et al., Expert opin. Ther. Patents, "Allosteric modulators for the A1-adenosine receptor", 2004, vol. 14, pp. 71-79.*
Yan et al., Expert Opin. Emerging Drugs, "Adenosine receptor agonists: from basic medicinal chemistry to clinical development", 2003, vol. 8, pp. 537-576.*
Francis, J.E., et al., "A general synthesis of 5,7-diaminoimidazo[4,5-b]pyridine ribosides ("2-amino-1-deazaadenosines") from 5-amino-4-imidazolecarboxamide riboside (AICA riboside)," Canadian J. Chem. 70, pp. 1288-1295, (1992).
Camaioni, E., et al., "New Substituted 9-Alkylpurines as Adenosine Receptor Ligands," Bioorganic & Medicinal Chemistry 6(5), pp. 523-533 (1998).
Wanner, M.J., et al., "2-Nitro Analogues of Adenosine and 1-Deazaadenosine: Synthesis and Binding Studies at the Adenosine $A_1$, $A_{2A}$ and $A_3$ Receptor Subtypes," Bioorganic & Medicinal Chemistry Letters, vol. 10, No. 18, pp. 2141-2144 (2000).
Sullivan, G.W., et al., "Cyclic AMP-dependent inhibition of human neutrophil oxidative activity by substituted 2-propynlcyclohexyl adenosine $A_{2A}$ receptor agonists," British Journal of Pharmacology, vol. 132, No. 5, (Mar. 3, 2001), pp. 1017-1026 (XP002322595).
Niiya et al., "2-(N'-Alkylidenehydrazino) Adenosines: Potent and Selective Coronary Vasodilators," Journal of Medicinal Chemistry, vol. 35, No. 24, (1992), pp. 4557-4561.
Medicinal Chemistry: "Principles and Practice," (1994), ISBN 0-85186-494-5, Ed.: F.D. King, p. 215.
Stella, J., "Prodrugs As Therapeutics," Expert Opin. Ther. Patents, 14(3), pp. 277-280 (2004).
Ettmayer, P., et al., "Lessons Learned from Marketed and Investigational Prodrugs," J. Med. Chem., 47 (10), pp. 2393-2404, (2004).
Cristalli et al., "Improved Synthesis and Antitumor Activity of 1-Deazaadenosine" J. Med. Chem. (1987), 30, pp. 1686-1688.
Itoh et al., "Studies on the Chemical synthesis of Potential Antimetabolites Regioselective Introduction of a Chlorine Atom into the Imidazo [4,5-b]pyridine Nucleus (1)," J. Heterocyclic Chem. (1982), 19, pp. 513-517.

(Continued)

*Primary Examiner*—Margaret D. Seaman
*Assistant Examiner*—Niloofar Rahmani
(74) *Attorney, Agent, or Firm*—Finnegan, Henderson, Farabow, Garrett & Dunner, L.L.P.

(57) ABSTRACT

The present invention relates to 2-substituted-1-deaza purine derivatives as adenosine receptor modulating agents, to methods for the preparation of these compounds and to novel intermediates useful for the synthesis of said purine derivatives.

The compounds have the general formula (1)

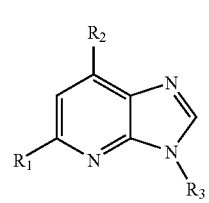

(1)

wherein the symbols have the meanings given in the specification.

13 Claims, No Drawings

OTHER PUBLICATIONS

Deghati et al., "Mild and Regioselective Nitration of 1-deazapurine Nucleosides using TBAN/TFAA," Tetrahedron Letters (2000), 41, pp. 569-573.

Wanner et al., "Synthesis and Properties of 2-nitrosoadenosine," J. Chem. Soc. Perkin Trans 1, (2001), pp. 1908-1915.

Townsend, A., et al., "A Threonine Residue in the Seventh Transmemebrane Domain of the Human $A_1$ Adenosine Receptor Mediates Specific Agonist Binding," Biol. Chem., 269, p. 2373-2376 (1994).

Luthin, D.R., et al., "Characterization of Two Affinity States of Adenosine $A_{2a}$ Receptors with a New Radioligand, 2-[2-(4-Amino-3-[$^{125}$I]iodophenyl)ethylamino]adenosine," Mol. Pharmacol., 47, p. 307 (1995).

Stehle, J.H., et al., "Molecular Cloning and Expression of the cDNA for a Novel $A_2$-Adenosine Receptor Subtype," Mol. Endocrinol., 6, p. 384, (1992).

Salvatore, C.A., et al., "Molecular Cloning and Characterization of the Human $A_3$ Adenosine Receptor," Proc. Natl. Acad. Sci. USA, 90, pp. 10365-10369 (1993).

Hess, S., "Recent Advances in Adenosine Receptor Antagonist Research", Expert Opin. Ther. Patents, 11, pp. 1547-1562, (2001).

Jacobsen, M.A., "Adenosine Receptor Agonists," Expert Opin. Ther. Patents, 12(4), pp. 489-501, (2002).

Cristalli, G., et al., II "Purine and Deazapurine n=Nucleosides: Synthetic Approaches, Molecular Modeling and Biological Activity," Farmaco, 58, pp. 193-204, (2003).

Klotz, K., et al., "9-Ethyladenine Derivatives as Adenosine Receptor Antagonists: 2- and 8-substitution results in distinct selectivities, Naunyn-Schmiedeberg's Archives of Pharmacology," 367, pp. 629-634 (2003).

Ginger-Sorolla, A., et al., "Fluorine-containing and Purines: Synthesis and Properties of Trifluoromethyl Pyrimidines and Purines$_1$," JACS 80, pp. 5744-5752, (1958).

Kaiser, C., et al., "A Synthesis of 2-Amino-6-trifluoromethylpurine," J. Org. Chem. 24, pp. 113-114, (1959).

Nagano, H., et al., "Fluorine-Containing Potential Anticancer Agents. II. $^{1a}$ Syntheses of Some Trifluoromethylpurines and Trifluoromethylthiazolopyrimidines $^{1b}$," J. of Med. Chem, Amer. Chem. Soc., vol. 7, no., pp. 215-220, (1964).

Kobayashi, Y., et al. "Studies on Organic Fluorine Compounds. Part 35.$^1$ Trifluoromethyl-ation of Pyrimidine- and Purine-nucleosides with Trifluoromethyl-Copper Complex," J. Chem. Soc. Perkin 1, pp. 2755-2761, (1980).

Green, A.R., et al., "The Effect of the C-6 Substituent on the Regioselectivity of N-Alkylation of 2-Aminopurines," Tetrahedron vol. 46, No. 19 pp. 6903-6914, (1990).

Hockova, D., et al., "Synthesis of Cytostatic Activity of Nucleosides and Acyclic Nucleoside Analogues Derived from 6-(Trifluoromethyl)purines," Tetrahedron 55, pp. 11109-11118, (1990).

Veliz, E.A., et al. "Synthesis and Analysis of RNA Containing 6-Trifluoromethylpurine Ribonucleoside," Organic Letters, vol. 3, No. 19, pp. 2969-2972 (2001).

Hocek, M., et al., "Perfluoraoalkylation of 6-Iodopurines By Trimethyl(Perfluoroalkyl)Silanes. Synthesis of 6-(Perfluoroalkyl)Purine Bases, Nucleosides and Acyclic Nucleotide Analogues," Collection of Czechoslovak Chemical Communications, 64, p. 229-241, (1999).

Ueeda, M. et al., "2-Alkoxyadenosines: Potent and Selective Agonists at the Coronary Artery $A_2$ Adenosine Receptor," J. Med. Chem., 34, pp. 1334-1339, (1991).

Rodenko, B., et al., "Solid Phase Synthesis of C2,$N^6$ -disubstituted adenosine analogues," J. Chem. Soc., Perkin Trans., 1, (2002), pp. 1247-1252.

Rodenko, B., et al., "The Mechanism of Selective Purine C-Nitration Revealed: NMR Studies Demonstrate Formation and Radical Rearrangement of an N7-Nitramine Intermediate," J. A.M. Chem. Soc., (2005), 127, pp. 5957-5963.

Gao Z.G., et al., "2-Substituted Adenosine Derivatives: Affinity and Efficacy at Four Subtypes of Human Adenosine Receptors," Biochemical Pharmacology 68 (2004) pp. 1985-1993.

Nanner, M.J., et al., "2-Nitro Analogues of Adenosine and 1-Deazaadenosine: Synthesis and Binding Studies at the Adenosine $A_1$, $A_{2A}$ and $A_3$ Receptor Subtypes," Bio. & Med. Chem. Letter, 10, pp. 2141-2144 (2000).

Search Report for PCT/EP2005/054405 dated Jan. 2, 2006.

Search Report for PCT/EP2005/054404 dated Jan. 16, 2006.

Co-pending U.S. Appl. No. 11/219,818, filed Sep. 7, 2005.

English language Derwent Abstract for JP 2004-217582.

* cited by examiner

2-SUBSTITUTED-1-DEAZA PURINE DERIVATIVES WITH ADENOSINE RECEPTOR MODULATING ACTIVITY

CROSS REFERENCE TO RELATED APPLICATION

This application claims the benefit of U.S. Provisional Application No. 60/608,145, filed Sep. 9, 2004, the content of which is incorporated herein by reference.

The present invention relates to 2-substituted-1-deaza purine derivatives as adenosine receptor modulating agents, to methods for the preparation of these compounds and to novel intermediates useful for the synthesis of said purine derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of disorders in which adenosine receptors are involved, or that can be treated via manipulation of those receptors.

At present, four types of adenosine receptors have been identified and designated $A_1$, $A_{2A}$, $A_{2B}$ and $A_3$ respectively. All four belong to the super-family of seven trans-membrane G-protein coupled receptors. Adenosine receptors are ubiquitous and involved in a great variety of biological processes. Thus, during the past decades the therapeutic potential of adenosine receptor ligands has resulted in a substantial research interest.

1-Deaza adenosines are known from EP 0 354 180 A, and were also described by J. E. Francis et al. (Canadian J. Chem. 70, 1288-1295, 1992) and M. J. Wanner et al. (Bioorganic & Medicinal Chemistry Letters 2000, 10, 2141-2144). These compounds were shown to have affinity for adenosine receptors, notably for the adenosine $A_2$ receptor subtype, on which they are agonists. The 1-deaza adenosines described in the documents cited above all contain the 9-β-D-ribofuranosyl substituent characteristic for the natural ligand adenosine. However, highly hydrophilic moieties like ribose have a negative impact on the bioavailability of compounds bearing such substituents.

The goal of the present invention was to develop 1-deazapurines without a ribose moiety, but with adenosine receptor modulating activity Surprisingly it was found that compounds of the general formula (1):

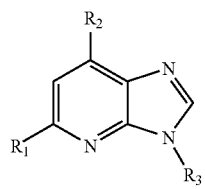

(1)

wherein $R_1$ represents oxa-3-azabicyclo[2.2.2]oct-5-en-3-yl, 4-hydroxy-cyclohexyl-NH—, optionally substituted arylalkyl($C_{1-3}$)amines, cycloalkyl($C_{3-8}$)alkyl-($C_{1-3}$)amines, arylalkyl($C_{1-3}$)hydrazines or cycloalkyl($C_{3-8}$)alkyl-($C_{1-3}$)hydrazines $R_2$ represents amino, NH-alkyl($C_{1-3}$) or N-dialkyl($C_{1-3}$) optionally substituted arylalkyl($C_{1-3}$)amines or cycloalkyl($C_{3-8}$)alkyl-($C_{1-3}$)amines, $R_3$ represents hydrogen, alkyl($C_{1-3}$) or arylalkyl($C_{1-3}$) and tautomers, stereoisomers, prodrugs and salts thereof, are new and are adenosine receptor modulators Throughout this specification the generally accepted atom numbering system of the purine skeleton is used:

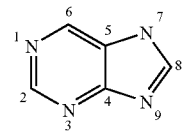

The invention relates to racemates, mixtures of diastereomers as well as the individual stereoisomers of the compounds having formula (1). The invention also relates to the E isomer, Z isomer and E/Z mixtures of compounds having formula (1). In the description of the substituents the abbreviation 'alkyl($C_{1-3}$)' means 'methyl, ethyl, n-propyl or iso-propyl'. 'Optionally substituted' means that a group may or may not be further substituted by one or more groups selected from alkyl, alkenyl, alkynyl, aryl, fluoro, chloro, bromo, hydroxyl, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. Within the context of the explanation of 'optionally substituted', 'alkyl' means $C_{1-3}$-alkyl, 'alkenyl' means $C_{1-3}$-alkenyl, 'alkynyl' means $C_{1-3}$-alkynyl, 'acyl' means $C_{1-3}$-acyl and 'aryl' means furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, 1,3,5-triazynyl, phenyl, indazolyl, indolyl, indolizinyl, isoindolyl, benzi[b]furanyl, benzo[b]thiophenyl, benzimidazolyl, benzthiazolyl, purinyl, quinolynyl, isochinolyl, chinolyl, phtalazinyl, quinazolinyl, quinoxalinyl, 1,8-naphthyridinyl, pteridinyl, naphthyl or azulenyl, preferably phenyl, pyridyl of naphthyl. Optional substituents may themselves bear additional optional substituents. Preferred optional substituents include $C_{1-3}$ alkyl such as for example methyl, ethyl, and trifluoromethyl, fluoro, chloro, bromo, hydroxyl, $C_{1-3}$ alkyloxy such as for example methoxy, ethoxy and trifluoromethoxy, and amino.

Prodrugs of the compounds mentioned above are in the scope of the present invention.

Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p.

215; J. Stella, "*Prodrugs as therapeutics*", Expert Opin. Ther. Patents, 14(3), 277-280, 2004; P. Ettmayer et al., "*Lessons learned from marketed and investigational pro-drugs*", J.Med.Chem., 47, 2393-2404, 2004).

Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The invention particularly relates to compounds of the general formula (1) in which:

$R_1$ represents oxa-3-azabicyclo[2.2.2]oct-5-en-3-yl, 4-hy-droxy-cyclohexyl-NH—, Ph-CH$_2$—CH=N—NH—, Ph-CH=N—NH—, 4-methoxy-Ph-CH=N—NH—, 2,4-dimethoxy-Ph-CH=N—NH—, cyclohexyl-CH$_2$—N=N— or cyclohexyl-CH=N—NH—, $R_2$ represents amino and $R_3$ represents methyl General Aspects of Syntheses The synthesis of compounds having formula (I) is outlined in Scheme 1. Modification and functionalization of the 2-position of the regular (1-aza)-purine ringsystem has received much attention. Substitution of purine-2-halides with amines proceeds often sluggish and requires high temperatures. The functionalisation of the 2-position in 1-deazapurines is even more difficult because it is a very deactivated system. An effective alternative is to start with 6-NO$_2$— or 6-Cl-substituted 1-deaza-purines. The synthesis of these starting materials is described by Cristalli et al. (J. Med. Chem. 1987, 30, 1686-1688) for X=NO$_2$, and by Itoh et al (J. Heterocyclic Chem. 1982, 19, 513-517) for X=Cl.

Scheme 1

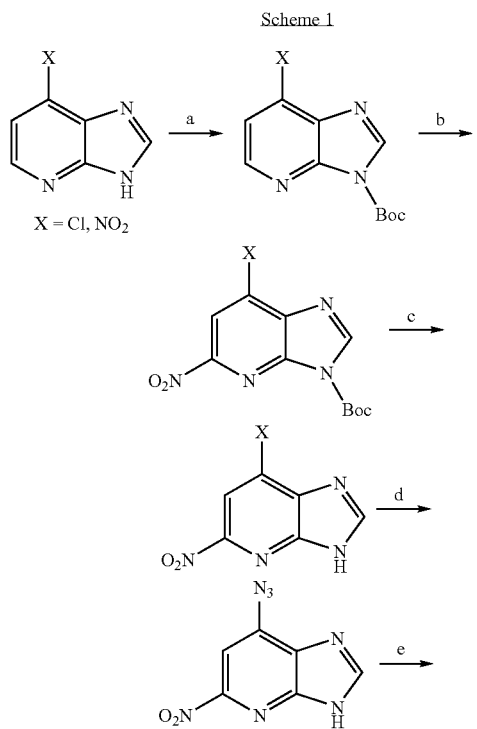

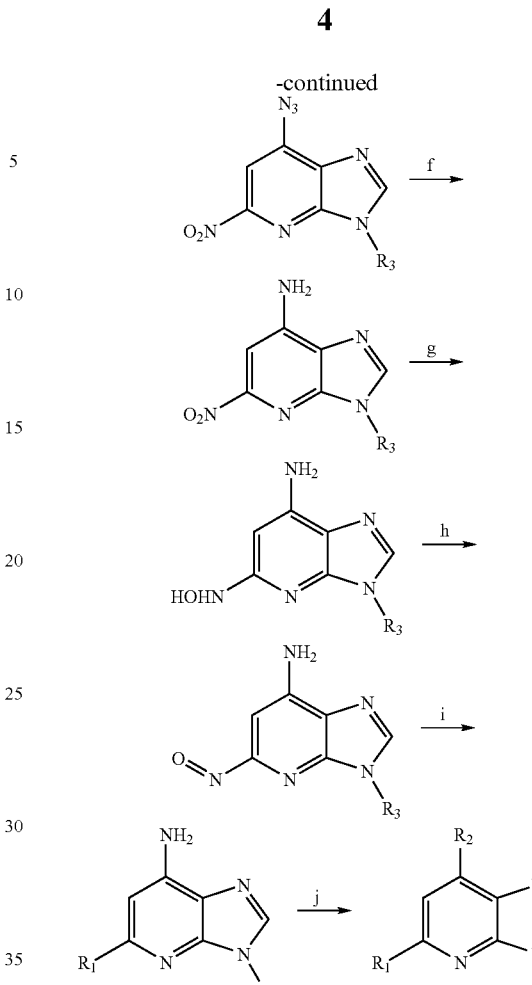

(a) Boc$_2$O; (b) TBAN/TFAA; (c) MeOH reflux (d) NaN$_3$; (e) substitution
(f) H$_2$/Pd/C (g) H$_2$ Pd/C, MeOH; (h)NaIO$_4$ oxidation; (i) functionalisation of 2-position;
(j) substitution 6-NH$_2$, leading to R$_2$ After BOC-protection selective nitration on the 2-position can be accomplished in an analogous way to the nitration of 9-ribose containing 1-deazapurines published by Deghati, Bieraugel, Wanner and Koomen (*Mild and regioselective nitration of 1-deazapurine nucleosides using TBAN/TFAA. Tetrahedron Letters* 2000, 41, 569-573). After a subsequent multi-step introduction sequence of a 2-nitroso moiety, the nitroso group can be further modified using Diels-Alder, ene reactions, addition reactions, Mills coupling, and condensation reactions. Additional information about the potential further modifications for analogous 2-nitrosoadenosines was published by Wanner and Koomen (*Synthesis and properties of 2-nitrosoadenosine. Journal of the Chemical Society-Perkin Transactions* 1, 2001, 1908-1915).

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid such as hydrochloric acid, or with an organic acid.

The compounds of the invention of the general formula (1), as well as the salts thereof, have adenosine receptor modulating activity. They are useful in the treatment of disorders in which adenosine receptors are involved, or that can be treated via manipulation of those receptors. For instance in: acute and chronic pain, inflammatory diseases including, arthritis, multiple sclerosis, asthma and psoriasis; gastro-intestinal disorders such as ulcers, inflammatory bowel disease (Crohn's disease) and ulcerative colitis; allergic responses such as eczema, atopic dermatitis and rhinitis; cardio-vascular disorders such as myocardial infarction, arrhythmias, hypertension, thrombosis, anaemia, arteriosclerosis, angina pectoris, cutaneous diseases such as urticaria, lupus erythematosus and pruritus; opthalmological disorders like glaucoma; respiratory disorders including chronic obstructive pulmonary disease, bronchitis and cystic fibrosis; central nervous system disorders including various forms of epilepsy, stroke, depression, sleep apnoea; disorders characterized by impairment of cognition and memory such as Alzheimer's disease, Creutzfeldt-Jacob disease, Huntington's disease, Parkinson's disease, neurorehabilitation (post-traumatic brain lesions); acute brain or spinal cord injury; diabetes, osteoporosis, diseases of the immune system, various carcinomas and leukemia, bacterial and viral infections.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. The invention also includes the preparation or manufacture of said pharmaceutical compositions.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Pharmacological Methods

In vitro Affinity for Human Adenosine-$A_1$ Receptors

Affinity of the compounds for human adenosine-$A_1$ receptors was determined using the receptor binding assay described by A. Townsend-Nicholson and P. R. Schofield (Biol. Chem., 269, 2373, 1994), using human recombinant receptors expressed in CHO cells, and [$^3$H]DPCPX as radioligand.

In vitro Affinity for Human Adenosine-$A_{2A}$ Receptors

Affinity of the compounds for human adenosine-$A_{2A}$ receptors was determined using the receptor binding assay described by D. R. Luthin et al. (Mol. Pharmacol., 47, 307, 1995), using human recombinant receptors expressed in HEK-293 cells, and [$^3$H]CGS 21680 as radioligand.

In vitro Affinity for Human Adenosine-$A_{2B}$ Receptors

Affinity of the compounds for human adenosine-$A_{2B}$ receptors was determined using the receptor binding assay described by J. H. Stehle et al. (Mol. Endocrinol., 6, 384, 1992), using human recombinant receptors expressed in HEK-293 cells, and [$^3$H]MRS 1754 as radioligand.

In vitro Affinity for Human Adenosine-$A_3$ Receptors

Affinity of the compounds for human adenosine-$A_3$ receptors was determined using the receptor binding assay described by C. A. Salvatore et al.: "*Molecular cloning and characterization of the human $A_3$ adenosine receptor*", Proc. Natl. Acad. Sci. USA, 90, 10365-10369, 1993. Briefly, membrane preparations were obtained from human recombinant (HEK 293) cells in which the human adenosine-$A_3$ receptor was stably expressed. Membranes were incubated at 22° C. for 90 minutes with [$^{125}$I]-AB-MECA in the absence or presence of test compounds in a concentration range from 10 μM down to 0.1 nM, diluted in a suitable buffer. Separation of bound radioactivity from free was done by filtration through Packard GF/B glass fiber filters with several washings with ice-cold buffer using a Packard cell harvester. Bound radioactivity was measured with a scintillation counter (Topcount, Packard) using a liquid scintillation cocktail (Microscint 0, Packard). Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_I$ values were calculated by correcting the $IC_{50}$ values for radioligand concentration and its affinity for the human adenosine-$A_3$ receptor according to the Cheng-Prusoff equation:

$$pK_I = -\log(IC_{50}/(1+S/K_d))$$

in which the $IC_{50}$ is as described above, S is the concentration [$^{125}$I]-AB-MECA used in the assay expressed in mol/l (typically 0.1 nM), and $K_d$ is the equilibrium dissociation constant of [$^{125}$I]-AB-MECA for human adenosine-$A_3$ receptors (0.22 nM).

The compounds of the invention have affinity for at least one of the adenosine receptors in one of the binding assays described above. These properties make them useful in the treatment of disorders in which adenosine receptors are involved, or that can be treated via manipulation of these receptors.

According to the procedures described above the compounds of the invention can be prepared. The examples are intended to further illustrate the invention in more detail, and therefore are not deemed to restrict the scope of the invention in any way.

Dose

The affinity of the compounds of the invention for adenosine $A_3$ receptors was determined as described above. From the binding affinity measured for a given compound of formula (1), one can estimate a theoretical lowest effective dose. At a concentration of the compound equal to twice the measured $K_i$-value, nearly 100% of the adenosine $A_3$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

Treatment

The term "treatment" as used herein refers to any treatment of a human condition or disease and includes: (1) preventing the disease or condition from occurring in a subject which may be predisposed to the disease but has not yet been diagnosed as having it, (2) inhibiting the disease or condition, i.e., arresting its development, (3) relieving the disease or condition, i.e., causing regression of the condition, or (4) relieving the conditions caused by the disease, i.e., stopping the symptoms of the disease.

EXAMPLES

Example 1

Materials and Methods

All reactions involving moisture sensitive compounds were carried out under a dry nitrogen atmosphere. Dichloromethane (phosphorous pentoxide and calciumhydride), tetrahydrofuran (sodium/benzophenone ketyl) and light petroleum (60-80) were distilled freshly prior to use. All other commercially available chemicals were used without further purification. Reactions were monitored by using thin-layer chromatography (TLC) on silica coated plastic sheets (Merck silica gel 60 F254) with the indicated eluent. The compounds were visualised by UV light (254 nm) or $I_2$. Flash chromatography refers to purification using the indicated eluent and Acros silica gel (0.030-0.075 mm). Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, unless indicated otherwise. $^{19}$F NMR and $^{13}$C NMR experiments were carried out on a Varian Inova 500 spectrometer operating at 11.74 T (499.9 MHz for $^1$H; 125.7 MHz for $^{13}$C; 50.7 Mhz, 470.4 MHz for $^{19}$F) using a 5 mm SW probe. The spectra were determined in deuterated chloroform or dichloromethane obtained from Cambridge Isotope Laboratories Ltd. Chemical shifts (δ) are given in ppm downfield from tetramethylsilane (1H, 13C) or CCl3F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'bs' (broad singlet) and 'm' (multiplet). NH and OH signals were identified after mixing the sample with a drop of $D_2O$. Melting points were measured with a Büchi B-545 Melting Point apparatus. Mass spectra and accurate mass measurements were performed using a JEOL JMS-SX/SX 102 A Tandem Mass Spectrometer using Fast Atom Bombardement (FAB). A resolving power of 10,000 (10% valley definition) for high resolution FAB mass spectrometry was used. Extinction coefficients were determined with a HP 8453 UV-Vis spectrophotometer. Analytical HPLC was performed on a C18 column (Inertsil ODS-3, particle size 3 mm; 4.6 mm 50 mm) using the following elution gradient: linear gradient of 5% to 95% aqueous $CH_3CN$ containing 0.04% $HCO_2H$ over 5 min, then 95% aqueous $CH_3CN$ containing 0.04% $HCO_2H$ for 2 min at 2.0 ml min$^{-1}$. Products were detected at λ=254 nm.

Example 2

Syntheses of Intermediates

Intermediate A: 6-Chloro-9-Boc-1-deazapurine

To a solution of 6-chloro-1-deazapurine (10 g, 65.1 mmol, J. Heterocyclic Chem. 1982, 19, 513-517) and $BOC_2O$ (19.8 g, 91.2 mmol) in dry dichloromethane (100 ml) was added dimethylaminopyridine (0.5 g, 5 mass %) and the mixture was stirred at room temperature for 30 minutes. The reaction was quenched by adding silica and the mixture was filtered over hyflo. Evaporating the solvent yielded the crude product. Trituration with petroleum ether followed by treatment with ether yielded the product as a white solid (6.29 g, 76%), mp: 183.5° C. decomposition $^1$H NMR ($d_6$-DMSO) δ 8.89 (s, 1H, H-8), 8.47-8.46 (d, J 5.3 , 1H, H-2), 7.62-7.61 (1H, d, J 5.3, H-1), 1.66 ( s, 9H t-Bu).

Intermediate B: 2-nitro-6-chloro-9-Boc-1-deazapurine

A solution of 6-chloro-9-Boc-1-deazapurine (1 g, 3.94 mmol, intermediate A) and tetrabutyl-ammonium nitrate (1.8 g, 5.91 mmol) in dry dichloromethane (12 ml) was stirred in an ice bath. TFAA (835 µL, 5.91 mmol) was added dropwise. After 1.5 h the reaction was complete and MeOH (20 ml) was added. The mixture was concentrated and cooled to give yellow crystals. The crude product was washed with 3×3 ml cold MeOH. Drying in vacuo at 50° C. afforded the product (0.916 g, 78%) as yellow needles. mp: 288.2-290° C. decomposition $^1$H NMR ($d_6$-DMSO) δ 9.22 (s,1H, H-8), 8.58 (s, 1H, H-1), 1.68 (s, 9H, t-Bu).

Intermediate C: 2-nitro-6-chloro-1-deazapurine 2-nitro-6-chloro-9-Boc-1-deazapurine (1.0 g, 3.35 mmol, intermediate B) in MeOH (20 ml) was stirred at 70° C. After 2 h the product started to precipitate. After 15 h the suspension was cooled at 0° C. for 30 min and filtered. The precipitate was washed with cold MeOH and dried in vacuo at 50° C. to furnish the product (0.5 g, 76%) as a yellow solid. mp: 294.5° C.

$^1$H NMR($d_6$-DMSO) δ 14.20 (bs, 1H, H-9), 8.92 (s, 1H, H-8), 8.41 (d, 1H, H-1).

Intermediate D: 6-nitro-9-Boc-1-deazapurine

To a solution of 6-nitro-1-deazapurine (5 g, 30 mmol, J.Med.Chem., 1987, 30, 1686-1688) and $BOC_2O$ (10 g, 46 mmol) in dry dichloromethane (100 ml) was added dimethylaminopyridine (0.250 g, 5 mass %) and the mixture was stirred at room temperature for 1.5 h. The reaction was diluted with PE and quenched by adding silica and the mixture was filtered over hyflo. Evaporating the solvent yielded the crude product. Crystallization with EA/PE afforded the product (2.28 g, 72%) as light yellow needles. mp: 223-226° C.

$^1$H NMR (d$_6$-DMSO) δ 9.11 (s, 1H, H-8), 8.81 (d, J 5.3, 1H, H-2), 8.10 (d J 5.3, 1H, H-1), 1.67 ( s, 9H t-Bu).

Intermediate E: 2,6-dinitro-1-deazapurine

A solution of 6-nitro-9-Boc-1-deazapurine (4 g, 15 mmol, intermediate D) and tetrabutylammoniumnitrate (0.92 g, 23 mmol) in dry dichloromethane (5 ml) was stirred at −18° C. TFAA (430 μL, 18 mmol) was added dropwise. After 1.5 h the nitration reaction was complete and MeOH (20 ml) was added. The solution was refluxed for 15 h while the product precipitates. Cooling and filtering and drying the suspension furnished the pure product (2.28 g, 72%) as light yellow crystals. mp: 294° C.

$^1$H NMR (d$_6$-DMSO) δ 14.45(bs, 1H, H-9), 9.16(s, 1H, H-8), 8.81 (d, 1H, H-1).

Intermediate F: 2-nitro-6-azido-1-deazapurine

First possible route: a suspension of 2-nitro-6-chloro-1-deazapurine (12 mmol, intermediate C) and NaN$_3$ (2.5 g, 37 mmol) in dry DMF (25 ml) was stirred and warmed to 60° C. After 60 h the reaction was cooled to room temperature and water was added slowly (100 ml). The product precipitated and was filtered. Washing with water and ether, followed by drying in vacuo at 50° C. furnished the product (2.12 g, 82%) as a solid.

Alternative route: a suspension of 2,6-dinitro-1-deazapurine (2.5 g, 12 mmol, intermediate E) and NaN$_3$ (2.4 g, 37 mmol) in dry DMF (20 ml) was stirred at room temperature for 3 h. After completion, water was added slowly (100 ml). The product precipitated and was filtered. Washing with water and ether, followed by drying in vacuo at 50° C. furnished the product (2.22 g, 90%) as a off white solid. mp: 220-224 ° C. decomposition $^1$H NMR(d$_6$-DMSO) δ 14.02 (bs, 1H, H-9), 8.78 (s, 1H, H-8), 7.81 (s, 1H, 1-H).

Intermediate G:
2-nitro-6-azido-9-methyl-1-deazapurine

To a suspension of 2-nitro-6-azido-1-deazapurine (6 g, 29.2 mmol, Intermediate F) and K$_2$CO$_3$ (8.09 g, 58.5 mmol) in dry DMF (150 ml) was added MeI (3.65 ml, 58.5 mmol). After 1 h the reaction was complete and water (300 ml) was added slowly. The product precipitated and the suspension was cooled in an ice-bath. The crude product was washed with water and ether and dried in vacuo at 50° C. to yield 5.61 g (88%) of the desired product as a white solid. mp: 171.7° C. decomposition $^1$H NMR (d$_6$-DMSO) δ 8.77 (s, 1H H-8), 7.80 (s, 1H, H-1), 3.92 (s, 3H, CH$_3$).

Intermediate H:
2-nitro-6-amino-9-Me-1-deazapurine

To a solution of 2-nitro-6-azido-9-methyl-1-deazapurine (1 g, 4.5 mmol, Intermediate G) was added Pd/C 10% (0.200 g, 20 mol %). The solution was stirred at room temperature under a H$_2$ atmosphere. After 1 h the reaction was complete. Flash chromatography (EA) of the crude reaction mixture afforded the pure product as a red solid (0.775 g. 88%). mp: 260-264° C.

$^1$H NMR (d$_6$-DMSO) δ 8.35 (s, 1H H-8), 7.36 (s, 1H, H-1), 7.15 (bs, 2H, NH$_2$), 3.79 (s, 3H, CH$_3$).

Intermediate I:
2-hydroxylamino-6-amino-9-methyl-1-deazapurine

A suspension of 2-nitro-6-azido-9-methyl-1-deazapurine (1 g, 45.6 mmol, Intermediate H) and 10% Pt/C (0.2 g, 20% m) in EA (200 ml) was refluxed under a H$_2$ athmosphere. After 18 h the reaction was filtered over Hyflo (EA/MeOH). The filtrate was used immediately for the oxidation reaction to the nitroso derivative.

$^1$H NMR (d$_6$-DMSO) δ 8.34 (s, 1H, H-8), 7.36 (s, 1H, H-1), 7.14 (bs, 2H, NH$_2$), 3.80 (s, 3H, CH$_3$).

Intermediate J:
2-nitroso-6-amino-9-methyl-1-deazapurine

The crude mixture of 2-hydroxylamino-6-amino-9-methyl-1-deazapurine (intermediate I) was cooled to 0° C. An ice-cold solution of NaIO$_4$ (1.95 g, 9.13 mmol) in H$_2$O (50 ml) was added slowly. After 1 h the reaction was complete and the organic layer was separated from the water layer. The aqueous layer was extracted with EA+5% MeOH and dried with Na$_2$SO$_4$. The yellow solution was concentrated and triturated with cold MeOH to yield 0.53 g (65%) of the desired product as a red solid. mp: 220° C.

$^1$H NMR (d$_6$-DMSO) δ 8.46 (s, 1H, H-8), 7.37 (s, 1H, H-1), 7.00 (bs, 2H, NH$_2$), 3.92 (s, 3H, CH$_3$)

Example 3

Syntheses of Specific Compounds

Compound 1: 2-(2-oxa-3-azabicyclo[2.2.2]oct-5-en-3-yl)-6-amino-9-methyl-1-deazapurine To a suspension of 2-nitroso-6-amino-9-methyl-1-deazapurine (0.1 g, 0.56 mmol, intermediate J) in MeOH (15 ml) was added slowly 1,3-cyclohexadiene (105 μl, 1.13 mmol). After 30 m the reaction was complete and the mixture was concentrated and triturated in cold MeOH. The product was washed with cold MeOH and dried at 50° C. in vacuo to yield 101.9 mg (75%) of the desired product as a white solid. mp: 169.9° C.

$^1$H NMR (d$_6$-DMSO) δ 7.82 (s, 1H, H-8), 6.52 (t, 1H, CH), 6.30 (t, 1H, CH), 6.12 (bs, 2H, NH$_2$), 5.99 (s, 1H, H-1), 5.21 (t, 1H, CH), 4.70 (t, 1H, CH), 3.63 (s, 3H, CH$_3$), 2.08 (q, 2H, CH$_2$), 1.55 (q, 2H, CH$_2$), 1.33 (q, 2H, CH$_2$); m/z 258.1355 (M$^+$+H. C$_{13}$H$_{16}$N$_5$O requires m/z 258.1277)

Compound 2: 2-(cis-4-hydroxycyclohexylamino)-6-amino-9-methyl-1-deazapurine

A suspension of 2-(2-oxa-3-azabicyclo[2.2.2]oct-5-en-3-yl)-6-amino-9-methyl-1-deazapurine (50 mg, 0.194 mmol, compound 1) and 10% Pd/C in MeOH (4 ml) was stirred under 1 atm hydrogen for 1.5 h at 70 ° C. Filtration, evaporation and stirring in cold MeOH afforded the pure 2-(cis-4-hydroxycyclohexylamino)-6-amino-9-methyl-1-deazapurine (23,8 mg, 47%) as white solid.

$^1$H NMR (d$_6$-DMSO) δ 7.62 (s, 1H, 8-H), 5.72 (s, 2H, NH$_2$), 5.69-5.67 (m, 1H, NH), 5.57 (s, 1h, 1-H), 4.34 (s, 1H, OH), 3.69 (s, 2H), 3.57 (s, 3H, CH$_3$), 1.63 (m, 6H, cyclo), 1.53-151 (m, 2H, cyclo) m/z 262.1668 (M$^+$+H. C$_{13}$H$_{19}$N$_5$O requires m/z 262.1590)

Compound 3: 2-(2-phenylethyl-hydrazone)-6-amino-9-methyl-1-deazapurine

A mixture of 2-nitroso-6-amino-9-methyl-1-deazapurine (0.1 g, 0.565 mmol), 2-phenylethylamine (858 μl, 0.677 mmol) and acetic acid $CH_3COOH$ (64.6 μl, 1.13 mmol) was stirred in MeOH. After 3 h the suspension had dissolved. The yellow solution was concentrated and diluted with PE and purified by flash chromatography (EA/MeOH/$NH_4OH$ 88.5:10:1.5). The product was triturated with cold methanol and dried in vacuo to yield 55.4 mg (35%) of the desired product as a yellow solid. mp: 182.1° C.
$^1$H NMR ($d_6$-DMSO) δ 10.07 (s, 1H, NH), 7.73 (s, 1H, 8-H), 7.37-7.32 (3H, m, CH/Ph), 7.27-7.25-7.23 (m, 3H, Ph), 6.28 (s, 1H, 1-H), 6.1 (bs, 2H, $NH_2$), 3.60 (s, 3H, $CH_3$), 3.56-3.54 (d, 2H, $CH_2$) m/z 281.1515 ($M^+$+H. $C_{13}H_{19}N_5O$ requires m/z 281.1436)

Compound 4: 2-benzylhydrazone-6-amino-9-methyl-1-deazapurine

Condensation of 2-nitroso-6-amino-9-methyl-1-deazapurine (0.1 g, 0.565 mmol), benzylamine (740 μl, 6.77 mmol) and acetic acid $CH_3COOH$ (64.6 μl, 1.13 mmol) was performed as described for compound 3. Flash chromatography (EA/MeOH/$NH_4OH$ 88.5:10:1.5). The product was triturated with cold methanol and dried in vacuo to yield 52.6 mg (35%) of the desired product as a yellow solid. mp: 231.7-232.8° C.;
$^1$H NMR ($d_6$-DMSO) δ 10.68 (s, 1H, NH), 7.95 (s, 1H, 8-H), 7.77 (s, 1H, CH), 7.64-7.62 (d, 2H, o-Ph), 7.41 (t, 2H, m-Ph), 7.31 (t, 1H, p-Ph), 6.46 (s, 1H, 1-H), 6.17 (bs, 2H, $NH_2$) m/z 267.1358 ($M^+$+H. $C_{13}H_{19}N_5O$ requires m/z 267.1280)

Compound 5: 2-(4-methoxy-2-benzylhydrazon)-6-amino-9-methyl-1-deazapurine

Condensation of 2-nitroso-6-amino-9-methyl-1-deazapurine (0.1 g, 0.565 mmol), 4-methoxy-benzylamine (369 μl, 2.82 mmol) and acetic acid $CH_3COOH$ (64.6 μl, 1.13 mmol) was performed as described for compound 3. Flash chromatography (EA/MeOH/$NH_4OH$ 94.5:5:0.5). The product was triturated with cold methanol and dried in vacuo to yield 58.5 mg (35%) of the desired product as a yellow solid.
$^1$H NMR ($d_6$-DMSO) δ 10.39 (s, 1H, NH), 7.91 (s, 1H, 8-H), 7.75 (s, 1H, CH), 7.56 (d, J 8.53 Hz, 2H, m-Ph), 6.98 (d, J 8.52 Hz, 2H, o-Ph), 6.42 (s, 1H, 1-H), 6.13 (bs, 2H, $NH_2$), 3.80 (s, 3H, $OCH_3$), 3.64 (s, 3H, $CH_3$) m/z 297.1464. ($M^+$+H. $C_{13}H_{19}N_5O$ requires m/z 297.3271

Compound 6: 2-(2,4-dimethoxy-2-benzylhydrazon)-6-amino-9-methyl-1-deazapurine Condensation of 2-nitroso-6-amino-9-methyl-1-deazapurine (0.075 g, 0.423 mmol), 2,4-dimethoxy-benzylamine (318 μl, 2.12 mmol) and acetic acid $CH_3COOH$ (48.4 μl, 0.847 mmol) was performed as described for compound 3. Flash chromatography (EA/MeOH/$NH_4OH$ 94.5:5:0.5). The product was triturated with cold methanol and ether and dried in vacuo to yield 48.3 mg (35%) of the desired product as a off white solid.
$^1$H NMR ($d_6$-DMSO) δ 10.38 (s, 1H, NH), 8.17 (s, 1H, 8-H), 7.78-7.75 (s, 2H, CH and 1-H), 6.61-6.6 (m, 2H, Ph), 6.40 (s, 1H, Ph), 6.11 (bs, 2H, $NH_2$), 3.85 (s, 3H, $OCH_3$), 3.82 (s, 3H, $OCH_3$), 3.63 (s, 3H, $CH_3$) m/z 327.1569 ($M^+$+H. $C_{13}H_{19}N_5O$ requires m/z 327.3531

Compound 7: 2-cyclohexylmethylazo-6-amino-9-methyl-1-deazapurine

Condensation of 2-nitroso-6-amino-9-methyl-1-deazapurine (0.1 g, 0.565 mmol), cyclohexylmethylamine (367 μl, 2.82 mmol) and acetic acid $CH_3COOH$ (64.6 μl, 1.13 mmol) was performed as described for compound 3. Flash chromatography (EA/MeOH/$NH_4OH$ 94.5:5:0.5). The product was triturated with ether and dried in vacuo to yield 72.6 mg (48%) of the desired product as a bright yellow solid.
$^1$H NMR ($d_6$-DMSO) δ 9.81 (s, 1H, NH), 7.71 (1H, s, 8-H), 7.17 (d J 5.31 Hz, 1H, CH), 6.22 (s, 1H, 1-H), 6.04 (s, 2H, $NH_2$), 3.6 (s, 3H, $CH_3$), 2.18-2.17 (m, 1H, cyclohexyl), 1.8-1.76-1.71 (m, 5H, 5×CH) 1.29-1.18 (m, 5H, CH) m/z 273.1828 ($M^+$+H. $C_{13}H_{19}N_5O$ requires m/z 273.1749

Compound 8: 2-(cyclohexylmethyl-hydrazone)-6-amino-9-methyl-1-deaza-purine 2-cyclohexylmethylazo-6-amino-9-methyl-1-deazapurine (0.03 g, 0.111 mmol, compound 7) was dissolved in EtOH (5 ml) and a catalytic amount of $N(Et)_3$ The mixture was refluxed overnight. The mixture was concentrated in vacuo, triturated with cold ether and MeOH and filtered producing 8 mg (27%) of the desired product as a yellow solid.
$^1$H NMR ($d_6$-DMSO) δ 9.81 (s, 1H, NH), 7.71 (s, 1H, 8-H), 7.16 (d, J 4.91 Hz, 1H, CH), 6.22 (s, 1H, 1-H), 6.04 (s, 2H, $NH_2$), 3.6 (s, 3H, $CH_3$)

TABLE I

Structural variations of compounds 1-8

| Compound | $R_1$ | $R_2$ | $R_3$ |
| --- | --- | --- | --- |
| 1 | 2-oxa-3-azabicyclo[2.2.2]oct-5-en-3-yl | $NH_2$ | $CH_3$ |
| 2 | 4-hydroxy-cyclohexyl-NH— | $NH_2$ | $CH_3$ |
| 3 | Ph—$CH_2$—CH=N—NH— | $NH_2$ | $CH_3$ |
| 4 | Ph—CH=N—NH— | $NH_2$ | $CH_3$ |
| 5 | 4-methoxy-Ph—CH=N—NH— | $NH_2$ | $CH_3$ |
| 6 | 2,4-dimethoxy-Ph—CH=N—NH— | $NH_2$ | $CH_3$ |
| 7 | Cyclohexyl-$CH_2$—N=N— | $NH_2$ | $CH_3$ |
| 8 | Cyclohexyl-CH=N—NH— | $NH_2$ | $CH_3$ |

Example 4

Formulation of Comp. 7 used in Animal Studies

For oral (p.o.) administration: to the desired quantity (0.5-5 mg) of the solid compound 7 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 7 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 5

Pharmacological Test Results

Adenosine receptor affinity data obtained according to the protocols given above are shown in the table below.

TABLE II

In vitro adenosine receptor affinity of compounds 1-8

| Compound | Adenosine receptor affinity | | |
|---|---|---|---|
| | $A_1$ $pK_i$ | $A_{2A}$ $pK_i$ | $A_3$ $pK_i$ |
| 1 | —.— | 4.8 | —.— |
| 2 | —.— | 5.1 | —.— |
| 3 | 5.6 | 5.5 | —.— |
| 4 | 5.4 | 5.9 | 5.6 |
| 5 | —.— | 6.0 | —.— |
| 6 | 5.2 | 5.7 | —.— |
| 7 | 6.0 | 6.1 | —.— |
| 8 | 5.5 | 5.7 | —.— |

The invention claimed is:

1. A compound of formula (1)

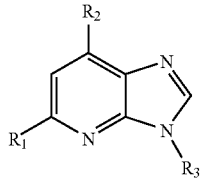

or a pharmaceutically acceptable salt, a stereoisomer, a tautomer, or a mixture of any of the foregoing wherein:
  $R_1$ is chosen from 2-oxa-3-azabicyclo[2.2.2]oct-5-en-3-yl, 4-hydroxy-cyclohexyl-NH—, and optionally substituted arylalkyl($C_{1-3}$)amines, cycloalkyl($C_{3-8}$)alkyl-($C_{1-3}$)amines, arylalkyl($C_{1-3}$) hydrazines and cycloalkyl($C_{3-8}$)alkyl ($C_{1-3}$)hydrazines;
  $R_2$ is chosen from amino, NH-alkyl($C_{1-3}$), N-dialkyl ($C_{1-3}$), and optionally substituted arylalkyl($C_{1-3}$) amines and cycloalkyl($C_{3-8}$)alkyl-($C_{1-3}$)amines; and
  $R_3$ is chosen from alkyl($C_{1-3}$), and arylalkyl($C_{1-3}$).

2. The compound according to claim 1, wherein
  $R_1$ is chosen from oxa-3-azabicyclo[2 2.2]oct-5-en-3-yl, 4-hydroxy-cyclohexyl-NH—, Ph-CH$_2$—CH=N—NH—, Ph-CH=N—NH—, 4-methoxy-Ph-CH=N—NH—, 2,4-dimethoxy-Ph-CH=N—NH—, cyclohexyl-CH$_2$—N=N— and cyclohexyl-CH=N—NH—;
  $R_2$ is an amino group; and
  $R_3$ is a methyl group.

3. The compound according to claim 1, wherein the compound of formula (1) is chosen from:
  2-(2-oxa-3-azabicyclo[2.2.2]oct-5-en-3-yl)-6-amino-9-methyl-1-deazapurine;
  2-(cis-4-hydroxycyclohexylamino)-6-amino-9-methyl-1-deazapurine;
  2-(2-phenylethyl-hydrazone)-6-amino-9-methyl-1-deazapurine;
  2-benzylhydrazone-6-amino-9-methyl-1-deazapurine;
  2-(4-methoxy-2-benzylhydrazon)-6-amino-9-methyl-1-deazapurine;
  2-(2,4-dimethoxy-2-benzylhydrazon)-6-amino-9-methyl-1-deazapurine;
  2-cyclohexylmethylazo-6-amino-9-methyl-1-deazapurine; and
  2-(cyclohexylmethyl-hydrazone)-6-amino-9-methyl-1-deaza-purine.

4. A pharmaceutical composition comprising:
  at least one pharmaceutically acceptable component chosen from a carrier, an auxiliary substance and combinations thereof; and
  a therapeutically effective amount of at least one compound of formula (1)

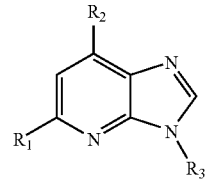

or pharmaceutically acceptable salts, a stereoisomer, a tautomer, or a mixture thereof, wherein:
  $R_1$ is chosen from 2-oxa-3-azabicyclo[2.2.2]oct-5-en-3-yl, 4-hydroxy-cyclohexyl-NH—, and optionally substituted arylalkyl($C_{1-3}$)amines, cycloalkyl($C_{3-8}$)alkyl-($C_{1-3}$)amines, arylalkyl($C_{1-3}$) hydrazines and cycloalkyl($C_{3-8}$)alkyl($C_{1-3}$)hydrazines;
  $R_2$ is chosen from amino, NH-alkyl($C_{1-3}$), N-dialkyl ($C_{1-3}$), and optionally substituted arylalkyl($C_{1-3}$) amines and cycloalkyl($C_{3-8}$)alkyl-($C_{1-3}$)amines; and
  $R_3$ is chosen from alkyl($C_{1-3}$), and arylalkyl($C_{1-3}$).

5. The pharmaceutical composition of claim 4, wherein:
  $R_1$ is chosen from oxa-3-azabicyclo[2.2.2]oct-5-en-3-yl, 4-hydroxy-cyclohexyl-NH—, Ph-CH$_2$—CH=N—NH—, Ph-CH=N—NH—, 4-methoxy-Ph-CH=N—NH—, 2,4-dimethoxy-Ph-CH=N—NH—, cyclohexyl-CH$_2$—N=N— and cyclohexyl-CH=N—NH—;
  $R_2$ is an amino group; and
  $R_3$ is a methyl group.

6. The pharmaceutical composition of claim 4, wherein the compound of formula (1) is chosen from:
  2-(2-oxa-3-azabicyclo[2.2.2]oct-5-en-3-yl)-6-amino-9-methyl-1-deazapurine;
  2-(cis-4-hydroxycyclohexylamino)-6-amino-9-methyl-1-deazapurine;
  2-(2-phenylethyl-hydrazone)-6-amino-9-methyl-1-deazapurine;
  2-benzylhydrazone-6-amino-9-methyl-1-deazapurine;
  2-(4-methoxy-2-benzylhydrazon)-6-amino-9-methyl-1-deazapurine;
  2-(2,4-dimethoxy-2-benzylhydrazon)-6-amino-9-methyl-1-deazapurine;
  2-cyclohexylmethylazo-6-amino-9-methyl-1-deazapurine; and 2-(cyclohexylmethyl-hydrazone)-6-amino-9-methyl-1-deaza-purine.

7. The composition according to claim 4, wherein the at least one pharmaceutically acceptable auxiliary substance is chosen from magnesium carbonate, titanium dioxide, lactose, mannitol and other sugars or sugar alcohols, talc, lactoprotein, gelatin, starch, cellulose and its derivatives, animal and vegetable oil, polyethylene glycol, mon- and polyhydric alcohol, and combinations thereof.

8. The composition according to claim 4, wherein the composition is in a form chosen from solutions, powders, tablets, capsules, ointments, and suppositories.

9. A method for preparing a pharmaceutical composition, comprising:
combining a pharmacologically active amount of at least one compound of formula (1)

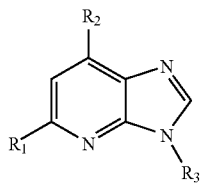

(1)

or pharmaceutically acceptable salts, a stereoisomer, a tautomer, or a mixture thereof, wherein:
$R_1$ is chosen from 2-oxa-3-azabicyclo[2.2.2]oct-5-en-3-yl, 4-hydroxy-cyclohexyl-NH—, and optionally substituted arylalkyl($C_{1-3}$)amines, cycloalkyl($C_{3-8}$)alkyl-($C_{1-3}$)amines, arylalkyl($C_{1-3}$) hydrazines and cycloalkyl($C_{38}$)alkyl($C_{1-3}$)hydrazines;
$R_2$ is chosen from amino, NH-alkyl($C_{1-3}$), N-dialkyl ($C_{1-3}$), and optionally substituted arylalkyl($C_{1-3}$) amines and cycloalkyl($C_{3-8}$)alkyl-($C_{1-3}$)amines; and
$R_3$ is chosen from alkyl($C_{1-3}$), and arylalkyl($C_{1-3}$) and
at least one pharmaceutically acceptable component chosen from a carrier, an auxiliary substance, and combinations thereof.

10. The method of claim 9, wherein:
$R_1$ is chosen from oxa-3-azabicyclo[2.2.2]oct-5-en-3-yl, 4-hydroxy-cyclohexyl-NH—, Ph-CH$_2$—CH=N—NH—, Ph-CH=N—NH—, 4-methoxy-Ph-CH=N—NH—, 2,4-dimethoxy-Ph-CH=N—NH—, cyclohexyl-CH$_2$—N=N— and cyclohexyl-CH=N—NH—;
$R_2$ is an amino group; and
$R_3$ is a methyl group.

11. The method of claim 9, wherein the at least one compound of formula (1) is chosen from:
2-(2-oxa-3-azabicyclo[2.2.2]oct-5-en-3-yl)-6-amino-9-methyl-1-deazapurine;
2-(cis-4-hydroxycyclohexylamino)-6-amino-9-methyl-1-deazapurine;
2-(2-phenylethyl-hydrazone)-6-amino-9-methyl-1-deazapurine;
2-benzylhydrazone-6-amino-9-methyl-1-deazapurine;
2-(4-methoxy-2-benzylhydrazon)-6-amino-9-methyl-1-deazapurine;
2-(2,4-dimethoxy-2-benzylhydrazon)-6-amino-9-methyl-1-deazapurine;
2-cyclohexylmethylazo-6-amino-9-methyl-1-deazapurine; and
2-(cyclohexylmethyl-hydrazone)-6-amino-9-methyl-1-deaza-purine.

12. The composition according to claim 9, wherein the at least one pharmaceutically acceptable auxiliary substance is chosen from magnesium carbonate, titanium dioxide, lactose, mannitol and other sugars or sugar alcohols, talc, lactoprotein, gelatin, starch, cellulose and its derivatives, animal and vegetable oil, polyethylene glycol, mon- and polyhydric alcohol, and combinations thereof.

13. The method of claim 9, wherein the pharmaceutical composition is in a form chosen from solutions, powders, tablets, capsules, ointments, and suppositories.

* * * * *

UNITED STATES PATENT AND TRADEMARK OFFICE
CERTIFICATE OF CORRECTION

PATENT NO. : 7,338,964 B2  Page 1 of 1
APPLICATION NO. : 11/219817
DATED : March 4, 2008
INVENTOR(S) : Koche et al.

It is certified that error appears in the above-identified patent and that said Letters Patent is hereby corrected as shown below:

On the title page, item (12), line 2, "Koche" should read --Koch--.

On the title page, item (75), line 1, "Koche," should read --Koch,--.

In claim 2, column 13, line 55, "oxa-3-azabicyclo[2 2.2]oct-5-en-3-yl," should read --oxa-3-azabicyclo[2.2.2]oct-5-en-3-yl,--.

In claim 9, column 15, line 34, "cycloalkyl($C_{38}$)alkyl($C_{1-3}$)hydrazines;" should read --cycloalkyl($C_{3-8}$)alkyl($C_{1-3}$)hydrazines;--.

Signed and Sealed this

Tenth Day of June, 2008

JON W. DUDAS
*Director of the United States Patent and Trademark Office*